United States Patent [19]

Meilus

[11] Patent Number: 5,666,964
[45] Date of Patent: Sep. 16, 1997

[54] MUSCLE TREATMENT DEVICES

[76] Inventor: Algis A. Meilus, 340 N. Tessier Dr., St. Petersburg, Fla. 33706

[21] Appl. No.: 470,402

[22] Filed: Jun. 6, 1995

[51] Int. Cl.⁶ ................................................. A61H 39/00
[52] U.S. Cl. ........................ 128/744; 128/774; 601/23; 601/134
[58] Field of Search ................... 128/774, 782, 128/744; 73/379.01, 379.02, 379.03, 379.04, 379.05, 379.08; 606/204; 601/23, 134, 135; 269/165, 166, 167, 274, 329

[56] References Cited

U.S. PATENT DOCUMENTS

| | | | |
|---|---|---|---|
| 3,008,239 | 11/1961 | Lange | 128/774 |
| 3,133,355 | 5/1964 | Gordon | 128/774 |
| 4,505,278 | 3/1985 | Alban | 128/774 |
| 4,742,832 | 5/1988 | Kauffmann et al. | 128/774 |
| 5,090,421 | 2/1992 | Wagoner, III | 128/774 |
| 5,183,055 | 2/1993 | Seager | 128/774 |
| 5,224,469 | 7/1993 | Mocny | 128/774 |
| 5,301,683 | 4/1994 | Durkan | 128/774 |

FOREIGN PATENT DOCUMENTS

| | | | |
|---|---|---|---|
| 268621 | 6/1989 | Germany | 128/774 |

*Primary Examiner*—Jeanne M. Clark
*Attorney, Agent, or Firm*—Dorothy S. Morse

[57] ABSTRACT

Muscle treating devices for use by muscular therapists and patients include a clamp device having utility as a muscle treating device. It includes a probe attached to a preselected movable jaw that simulates a therapist's fingers or thumb. It further includes a quick release device and a pressure measuring device so that a therapist can record pressures at which a patient reports discomfort. Additional muscle treating devices treat the cervical, thoracic, and lumbar regions of the back. Each of these devices includes a flat, rigid base and a support member disposed normal to the base having a groove formed in its peripheral edge for receiving neck vertebrae, the thoracic spine, and the lumbar spine, respectively. A combination device combines the cervical, thoracic, and lumbar devices into a single unit so that all of the muscles flanking the spinal column are treated simultaneously. Another device has an elongated inverted "V" structure and has utility for treating leg muscles, and still another device is a rigid or pivoting probe mounted in upstanding relation to a flat base and has utility in treating muscles of the lower back.

6 Claims, 6 Drawing Sheets

MUSCLE TREATMENT DEVICES

BACKGROUND OF THE INVENTION

1. Field of the Invention

This invention relates, generally, to devices having utility in the field of muscular therapy. More particularly, the devices assist a muscular therapists in treating large muscles, various spine muscles including low back muscles, leg muscles and the like. The devices may also be used by patients for home use.

2. Description of the Prior Art

Traditional muscular therapists practice their art with their hands, including their fingers, thumbs, palms, wrists, and employ other parts of their bodies as well, such as elbows, i.e., the whole body of the therapist gets involved in the treatment. As a result, the effectiveness of the therapist decreases as the day wears on, and uniformity of patient treatment is not assured.

Although there have been numerous devices developed to decrease the physical demands placed upon the therapist, none of them effectively treat the muscles of the cervical, thoracic, or lumbar regions, nor are there any devices that treat other large muscles of the body in such a that enables the therapist to easily adjust pressures and to diagnose various conditions of the patient.

In view of the prior art considered as a whole at the time the present invention was made, it was not obvious to those of ordinary skill in this art that better labor-saving devices were needed, or how the needed devices could be provided.

SUMMARY OF THE INVENTION

The longstanding but heretofore unfulfilled need for devices that assist a muscular therapist in treating large muscles as well as muscles of the cervical, thoracic, lumbar, and other regions is now met.

A first unique apparatus is a specially modified clamping device and has utility in applying pressure to large muscles or any place on the body where a clamping action is needed. The clamping surfaces in a first embodiment are flat, soft pads formed of rubber or other suitable nonslip or nonskid material. The pads are releasably attached to the metallic jaws of the clamp and are more suitable for contacting human skin than are said metallic jaws.

In a second embodiment, the pads are adapted so that various probe devices may be detachably mounted thereto. For example, in one configuration, a device that simulates a thumb or finger (or thumb and finger, e.g.) is attached to a first pad, and the opposing pad is a soft, flat pad of the type just mentioned. Thus, as the jaws of the clamp are brought toward one another, the thumb or finger-simulating device presses on the patient's muscle with an increasing amount of force. The energy required by the therapist to tighten the clamping action is less energy than would be required to perform the same action with the therapist's finger or thumb.

The probes may take many forms and may simulate a thumb and two index fingers, an elbow, and the like.

In another embodiment, each probe has a rigid base and a distal free end pivotally connected to the base. Thus, as the jaws of the clamp are converged, the pivotal free end of the probe adapts itself to the shape of the body surface it contacts, i.e., the distal free end of the probe self-positions itself upon contact with the patient's body.

The muscle clamping device further includes a pressure measuring means such as a strain gauge of the type used in various mechanical applications. The gauge has a first end secured to a nonmovable support surface and a second end is connected to the movable clamp jaw. The therapist increases the pressure on the patient's muscle until the patient announces that the pressure is causing discomfort. The therapist reads the strain gauge at that moment and records the reading to thereby indicate the state of the health of the patient's muscles at the time of the procedure.

The muscle clamping device has utility in applying pressure to the large muscles of the upper shoulders (the trapezious muscles), the broad muscles in the body such as in the upper and lower leg, any of the thin (about one-eighth of an inch) forearm flexors (for treating carpel tunnel discomfort), and any of the thinner muscles in the leg such as the peroneous longus; it also has utility in clamping numerous other small muscles. Moreover, it can also treat the subscapularis (under the shoulder blade), the iliacus (on the inside of the hip bone), or it may be used anywhere a clamping action across a muscle is needed, or where a patient must assume an odd position where support on an opposite side is required.

The invention further contemplates four devices that treat the muscles that attach to the spine. Specifically, the four devices are a cervical spinal muscle treatment device having a generally semicircular form, a thoracic spine device having an elongate extent and a gentle curvature, a lumbar muscle device having less extent than the thoracic spine device but more curvature than said thoracic spine device, and a whole spine device, having a length substantially coextensive with a spine, that combines the cervical, thoracic, and lumbar devices.

A pressure bar is a device that a muscular therapist uses to press down on muscles; these four devices mimic the application of pressure along the spine with such pressure bars, but provide an improvement over manual manipulation of such bars. Accordingly, the devices relax the muscles attached to the spine, realign vertebrae as muscles relax, and adjust vertebrae positions. Lying atop the spinal muscle treatment device, for example, often provides an instantaneous adjustment or "pop" of vertebrae that were out of place prior to treatment.

A leg spasm device includes a rounded surface that surmounts an A-shaped base. The device may statically support a leg along said rounded surface, or the patient can move his or her leg relative to said rounded surface.

The final device is a lower back/sciatica device. It includes several probe devices that simulate a finger, thumb, elbow, or the like. The probe is mounted on a base and is disposed in upstanding relation thereto so that it manipulates whatever muscle is positioned atop it. Advantageously, the probes used with the lower back treatment device are the same probes used with the large muscle treatment device.

All of the devices help conserve the energy of the therapist and provide uniformity of treatment. They are built of inexpensive materials and each of them has a simple mechanical structure so that they are easy to manufacture and therefore readily affordable by muscular therapists and patients for home use.

It should thus be understood that the primary object of this invention is to provide tools for muscular therapists that enhance the quality of the services provided by the therapists.

Another object is to reduce the physical demands placed upon practitioners of muscular therapy.

Still another object it to provide tools that enable muscular therapists to provide more uniform treatment to their patients.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
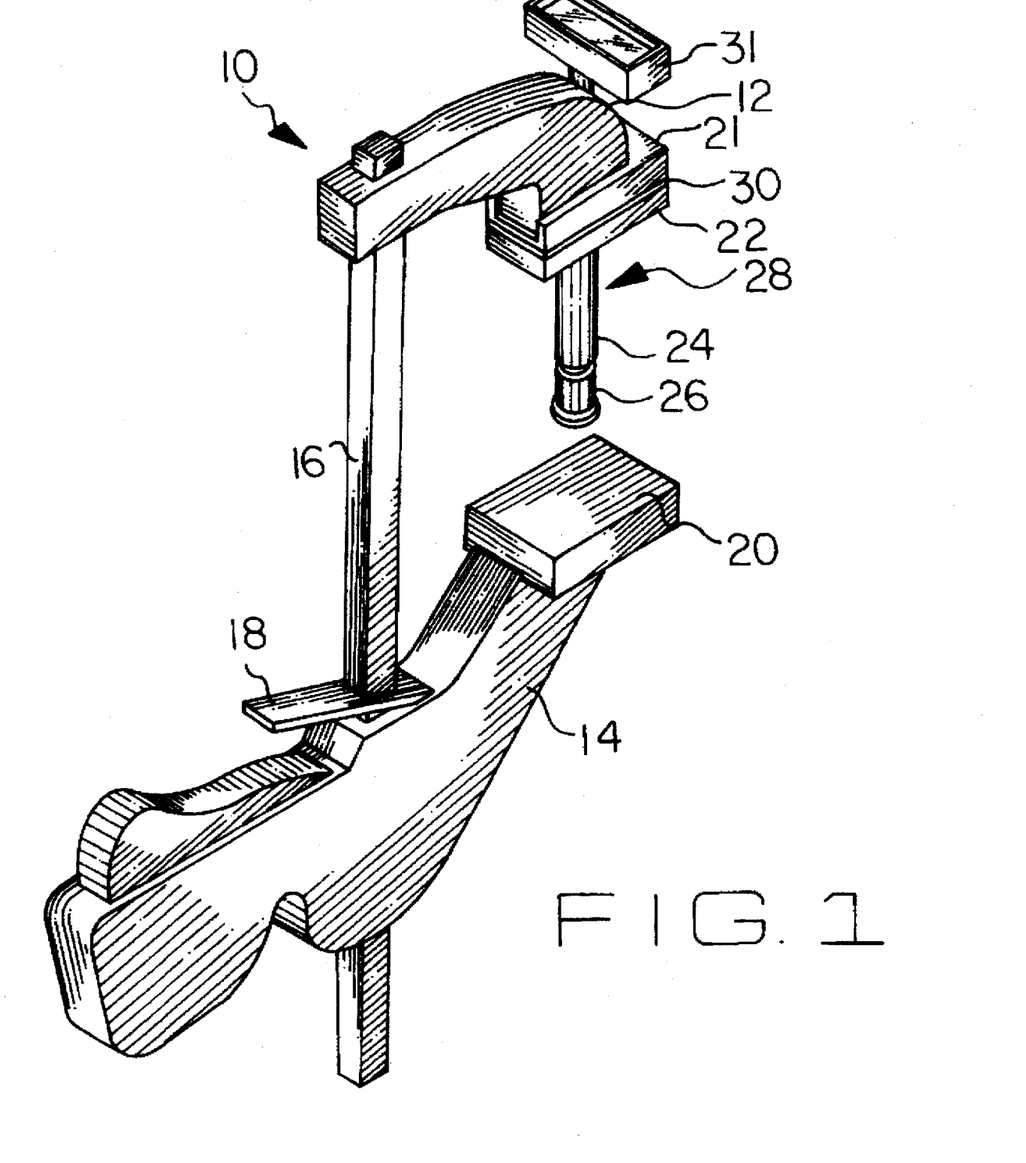
FIG. 1 is a side elevational view of a first embodiment of a large muscle clamping device.

Referring now to FIG. 1, it will there be seen that an illustrative embodiment of the invention is denoted as a whole by the reference numeral 10.

Muscle clamping device 10 includes a pair of opposed jaws 12 and 14 that are mounted on elongate base member 16. Handle 18 is a quick release device that separates the jaws from one another instantly when activated by squeezing or other manipulation. Quick release clamps of this type are well known and are widely available in hardware stores.

Device 10, in its commercially available configuration, has little or no utility, however, for gripping the human body because each jaw terminates in a flat metallic surface, as is well known, for securely gripping an inanimate object.

A relatively soft, flat pad 20 of rubber or other suitable, nonslip, nonskid material is releasably attached to jaw 14 so that said jaw is more suitable for contact with a human body. The same type of pad, denoted 21, is used to releasably cover the opposing jaw as well.

In a first embodiment, depicted in FIG. 1, a flat base 22 of more rigid structure is attached to or integrally formed with pad 21, and said base 22 has a centrally disposed bore formed therein to receive the proximal end of an upstanding rigid post 24, whether by press fitting, screw threading, or other form of releasable engagement. The distal free end of post 24 is adapted for releasable engagement with an applicator 26 which simulates a human fingertip. The post and applicator as a unit will be referred to hereinafter as probe 28.

This invention also teaches the replacement of applicator 26 with numerous other applicators that respectively simulate a human thumb, elbow, a thumb and a finger, a thumb and two fingers, and so on.

Figure 2:
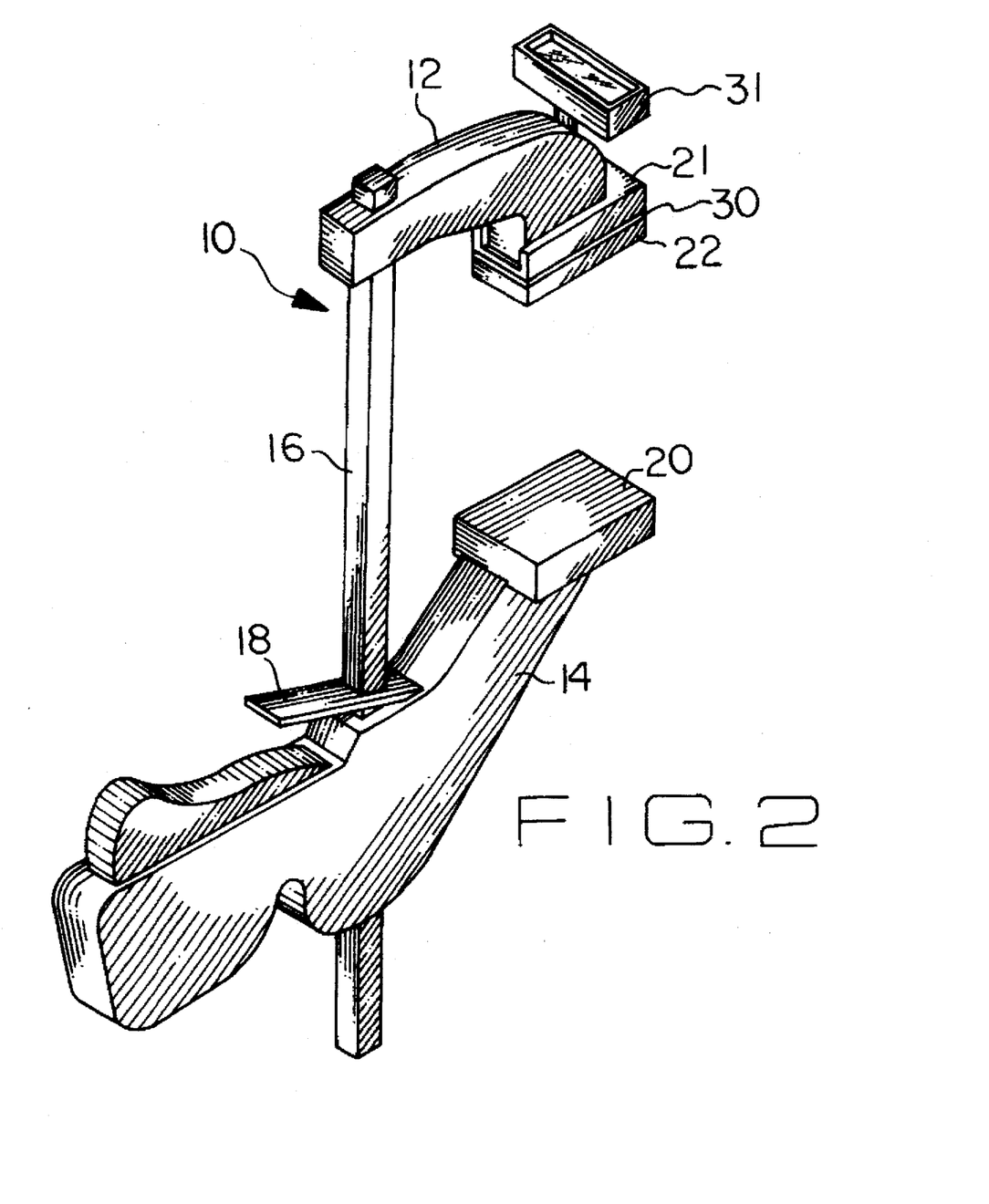
FIG. 2 is a side elevational view of a second embodiment thereof.

Applicator 26 may also be pivotally or swivally mounted to the distal end of post 24 so that it pivots and positions itself upon making contact with a patient's skin, and FIG. 2 should be interpreted as depicting such pivotal or swivel mounting.

FIGS. 1 and 2 also depict a strain gauge 30 mounted in sandwiched relation to jaw 12 and pad 21, and a display means 31 for reading the guage. Gauges of this type are used in many differing applications, but heretofore had not been used in connection with muscular therapy tools. For example, a hospital might use a strain gauge to weigh an empty bed so that the weight of a patient lying on said bed can be calculated.

Strain guage 30 may take the form of any pressure measuring device, including spring-loaded devices, air pressure devices, and other mechanisms that measure pressure.

In the treatment of certain muscles of a patient, a therapist uses tool 10 by positioning jaw 14 and probe 28 on opposite sides of the muscle to be manipulated. The jaws are then brought together gradually, and pressure is applied to said muscles. If the muscles being treated are healthy, they can handle high amounts of pressure, such as sixty pounds per square inch, in the absence of pain. In fact, blood vessels will rupture due to excessive pressure applied before a truly healthy muscle will generate pain impulses because a truly healthy muscle can handle very high pressures per square inch. However, patients with unhealthy muscles can experience pain even under one or two pounds per square inch of pressure, and some feel pain even when lightly touched. Accordingly, the therapist converges jaws 12 and 14 slowly, and requests the patient to speak up when discomfort is experienced. When pain is reported, the therapist reads strain gauge display means 31 and manipulates handle 18 to immediately separate the jaws from one another and to thereby immediately relieve the discomfort.

Information concerning how much pressure a muscle is able to withstand before generating pain signals is valuable diagnostic information. Before this invention, a therapist could make broad observations, such as patient Jones experiences pain with a small amount of pressure, patient Smith with a moderate amount, and so on, but more precise pressure threshholds of pain were unobtainable. This invention quantifies the pain threshhold and enables the therapist to make a precise written record of each patient's response to therapy over a period of time. Thus, the therapist can monitor a patient's condition from week to week as the patient withstands more and more (or less and less) pressure before reporting pain. Where no or little progress is being made, the therapist can alter the therapy.

Without the precise readings provided by the strain gauge, the therapist could continue for a prolonged period of time with ineffective therapy techniques due to the inability to accurately gauge a patient's progress. For example, the therapist might have a vague feeling that increasing amounts of pressure are being applied to a patient's muscles at each visit, but such vague feeling could be completely wrong.

The strain guage need not be positioned between jaw 12 and pad 21 exclusively; it may also be hand held, i.e., it may be positioned between the therapist's hand and the muscle being manipulated. The readings thereby obtained would have less accuracy, but would be better than no readings.

Figure 3:
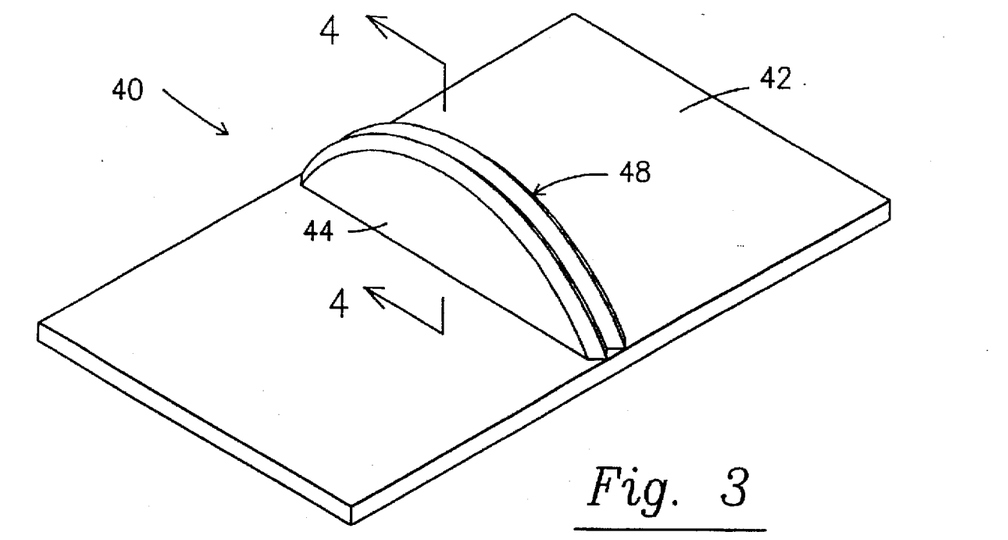
FIG. 3 is a perspective view of a cervical spine device.

Turning now to FIG. 3, it will there be seen that the novel cervical spine device is denoted by the reference numeral 40 as a whole. It includes a rigid flat base 42 in the form of a board or other suitable material, and a semicircular neck support 44 having a predetermined radius of curvature and a curved extent that is about the length of a human neck. As perhaps best understood in connection with FIG. 4, a groove 46 is formed in the curved peripheral edge 48 (FIG. 3) of support 44; parts 50, 52 are the parts of edge 48 that flank said groove 46. Thus, when the back of a patient's neck overlies neck support 44, transversely spaced apart parts 50, 52 support the neck without contacting the spinus processus of the vertabrae in the neck, i.e., the vertabrae are suspended over the bottom of groove 46. Parts 50, 52 thus perform the function of pressure bars.

Figures 4, 5:
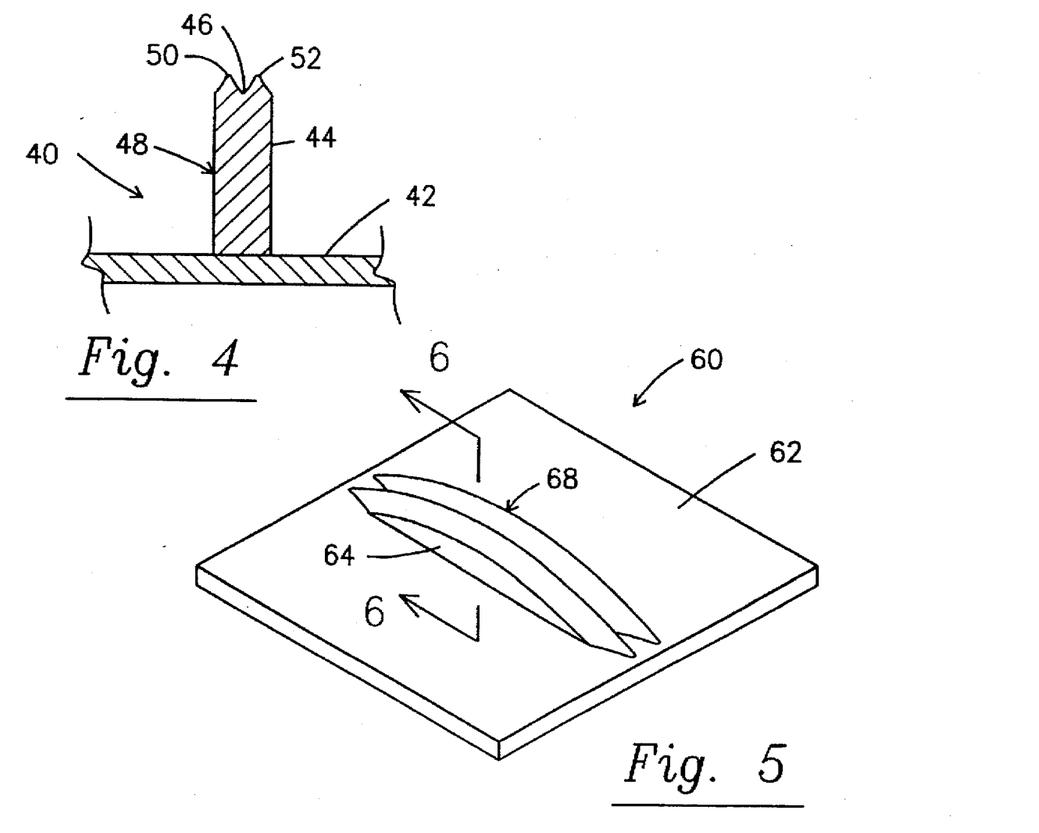
FIG. 4 is a sectional view taken along line 4—4 in FIG. 3.
FIG. 5 is a perspective view of a thoracic spine device.

Note that the curvature of cervical spine device 40 is shaped to conform to the shape of the cervical curve in a human neck. In a preferred embodiment, device 40 is provided in a small size and a large size, essentially for treating women and men, respectively. The small size has a length of about 4 inches and a radius of curvature of about 2½ inches; the larger size is about 5 inches in extent and has a radius of curvature of about 2½ inches.

Figure 6:
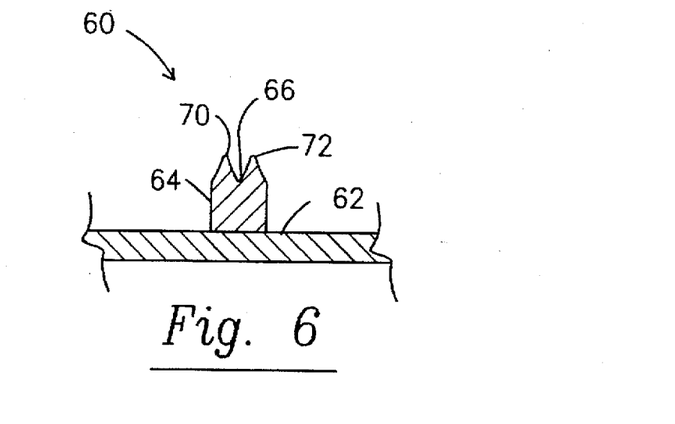
FIG. 6 is a sectional view taken along line 6—6 in FIG. 4.

The novel thoracic spine device is denoted 60 in FIGS. 5 and 6. It also includes a rigid, flat base 62 and a grooved support 64, but the longitudinal extent of support 64 is greater than that of the cervical device and is substantially equal to the extent of a typical human thoracic region. Groove 66 is formed in peripheral edge 68 (FIG. 5) and parts 70, 72 of said edge support the muscles on opposite sides of the thoracic spine without contacting the spinus processus of the vertabrae such that muscles attaching to either side of the spinus processus are treated.

Significantly, the shape of peripheral edge 68 is designed to slightly reverse the curve of the thoracic spine when a patient lies thereatop in a supine position. Thus, parts 70, 72 serve as pressure bars. The respective radii of curvature and lengths of a small and large version of device 60 is 12¾ inches, 12½ inches, and 19 inches, 22 inches, respectively.

Figures 7, 8:
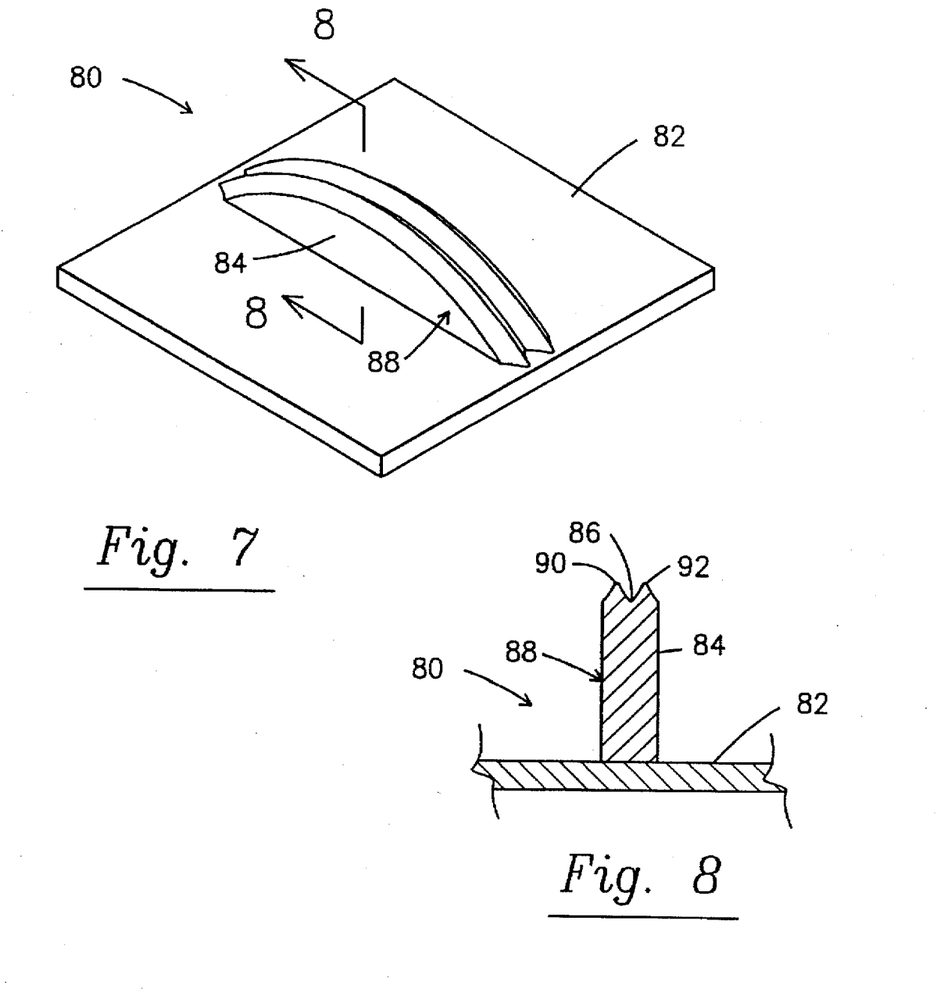
FIG. 7 is a perspective view of a lumbar spine device.
FIG. 8 is a sectional view taken along line 8—8 in FIG. 6.

Lumbar spine device, designed to place pressure on the muscles of the lower back when a person lies thereatop, is denoted 80 in FIGS. 7 and 8. It also includes a rigid, flat base 82 and a grooved support 84, but the longitudinal extent of support 84 is greater then that of the cervical device and less than that of the thoracic device; it is substantially equal to the extent of a typical human lumbar region. Groove 86 is formed in peripheral edge 88 and parts 90, 92 of said edge support the muscles on opposite sides of the lumbar spine without contacting the spinus processus of the spine.

Peripheral edge 88 is shaped to substantially conform to the shape of a human lower back. (12¾ inch radius of curvature, 7 inches in length for small version, 9 inch radius, 10 inch length for large version).

Figure 9:
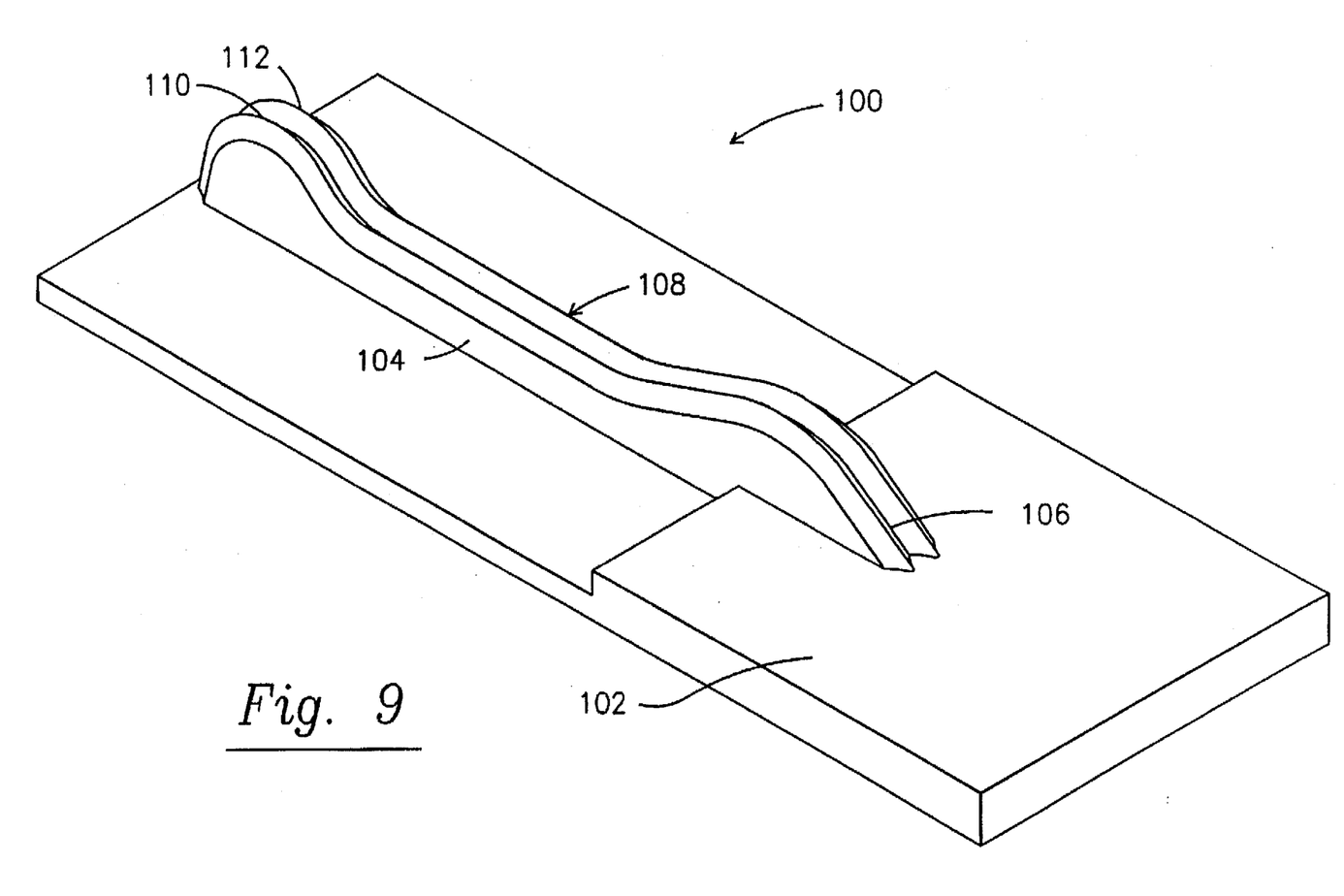
FIG. 9 is a perspective view of a whole spine device.

The novel whole spine device, designed to simultaneously place pressure on the muscles of the neck, thoracic region, and lower back when a person lies thereatop, is denoted 100 in FIG. 9. It includes a rigid, flat base 102 and a grooved support 104; the longitudinal extent of support 104 is substantially equal to the combined longitudinal extent of the cervical device 40, the thoracic device 60, and the lower back device 80. Groove 106 is formed in peripheral edge 108 and parts 110, 112 of said edge support the muscles on opposite sides of the neck and spine without contacting the spinus processus of the neck and spine.

Peripheral edge 108 is shaped to substantially conform to the shape of a human cervical region, thoracic region, and lower back. More particularly, the respective shapes of the cervical and lower back regions conform to the corresponding shapes of the human body, but in a preferred embodiment, the shape of the thoracic region slightly reverses the shape of the human thoracic region. Following the thoracic curve is also within the scope of this invention.

Figures 10, 11:
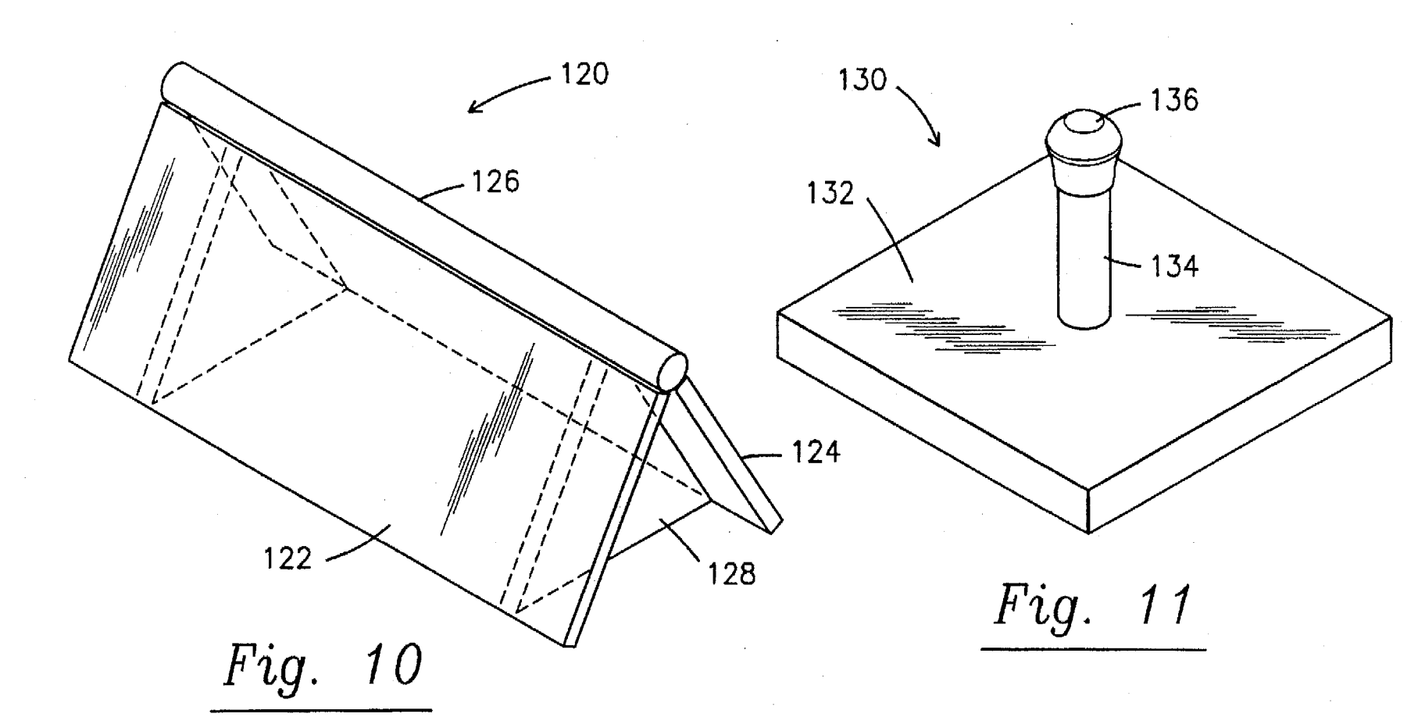
FIG. 10 is a perspective view of a leg spasm device.
FIG. 11 is a perspective view of a low back/sciatica device.

Leg spasm device 120, depicted in FIG. 10, is preferably an integrally formed piece having no moving parts. Flat, elongate sidewalls 122 and 124 are disposed in converging relation to one another and meet at a rounded apex 126. Cross bar 128 may be provided for structural integrity but its provision is not critical. A patient uses the device by resting the back of his or her leg atop the rounded apex 126, or by reciprocating the leg in a direction normal to the longitudinal axis of apex 126. The pressure is applied by the weight of the leg, and may be increased or decreased as desired by the patient by lifting the leg or pressing it down. The treatment afforded by device 120 is highly beneficial to runners and other athletes.

Low back/sciatica device 130, depicted in FIG. 11, includes a flat, rigid base 132 and a post 134 that terminates in an applicator 136. The probes usable with device 130 are the same probes usable with large muscle clamping device 10. All of the probes are used in substantially the same way, i.e., the patient lies down atop device 130, positioning the lower back over said device, and positions the lumbar region in registration with the probe. Alternatively, device 130 may be positioned against the back of a chair so that it may be used by a patient sitting in said chair.

All of these devices reduce the labor required of a muscular therapist without reducing the quality of care provided to the patient, and enable a patient to administer self-treatment as well.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A therapy device for simulating muscular therapy given manually by therapists wherein increasing pressures of up to sixty pounds of pressure are applied to a patient's muscles until the pain threshold of the patient is reached and for obtaining simultaneous quantified measurements of muscle hardness as a function of the amount of contraction in the muscles to measure progress of therapy so provided, said device comprising;

a clamp having a pair of opposed first and second laws that are movably mounted with respect to one another so as to move toward and away from one another, said clamp configured and made of materials sufficiently strong to be able to apply up to sixty pounds of pressure to muscles;

pressure measuring means associated with said first jaw of said clamp which quantitatively measures muscle hardness as a function of muscle contraction;

said clamp including a quick release means for releasing pressure applied by said jaws to muscles positioned therebetween;

a flat, soft pad releasably attached to said second jaw, said pad being made from non-slip material to prevent slippage of said second jaw against soft tissue; and a plurality of upstanding pointed probes for applying pressure perpendicular to the tissue being treated, said probes being releasably attached interchangeably to said first jaw in a position to perpendicularly oppose said second jaw, each of said probes having a rigid base, at least one of said probes having a distal free end configured to simulate muscular therapy performed by the pointed end of a human elbow, and at least one of said probes having a distal free end configured to simulate muscular therapy performed by single digit on a human hand so that pressures incrementally applied to a muscle positioned between said jaws as said jaws are converged toward one another stretches injured muscle tissue and promotes blood circulation and healing within the injured muscle tissue so that as it heals the injured muscle tissue can withstand increasingly more pressure without discomfort, and so that the mount of muscle hardness due to muscle contraction after each increment of said converting can be quantitatively measured by said pressure measuring means simultaneously during therapy to assess progress of said therapy.

2. The device of claim 1 wherein said distal free ends of said plurality of probes are movably mounted to said rigid base so that said distal free ends self-position upon coming into contact with a large muscle.

3. The device of claim 1, wherein said pressure measuring means comprises a strain gauge and a numerical display means connected to said strain gauge for compilation by a muscular therapist of a record of pressure readings taken from said pressure measuring means during therapy for diagnostic purposes.

4. A labor saving therapy device for self treatment and the treatment of others for incrementally applying up to sixty pounds of non-distributed, precise, tissue penetrating pressure to the greatest point of spasm in soft tissue of patients until the patients feel discomfort whereby muscle tissues in each successive layer of a muscle are made to lengthen and are able thereafter to withstand increasing amounts of additional pressure without pain and discomfort, and for simultaneous measuring of the hardness of soft tissues receiving therapy so as to quantify the progress of therapy provided by said device, said device comprising a first jaw and a second jaw, said first and second jaws being movably mounted with respect to one another so as to move toward and away from one another and form a clamp; a plurality of upstanding pointed probes, said probes being releasably attached interchangeably to said first jaw in a position to perpendicularly oppose said second jaw, at least one of said probes having a distal free end configured to simulate manual muscular therapy performed by the pointed end of a human elbow, and at least one of said probes having a distal free end configured to simulate manual muscular therapy performed by a single digit on a human hand; a quick release means for safety should pressure be inadvertently applied to a nerve or an artery, said quick release means being connected between said first and second jaw for quickly releasing pressure applied by one of said probes and said second jaw to soft tissue placed therebetween; a pressure measuring means connected to said first jaw; and a pad releasably attached to said second jaw to help reduce slippage of said second jaw against soft tissue of a patient so that pressure exerted on soft tissue placed between one of said probes and said second jaw provides more uniform therapy to soft tissue than therapy performed manually by a human therapist, provides self treatment with up to sixty pounds of pressure which would not be possible with manual therapy, provides therapy without fatigue to a therapist as would be experienced during manually performed therapy, and provides a simultaneous pressure measuring means for quantifying progress of said therapy.

5. The device of claim 4 wherein said jaws are made from metallic materials having sufficient strength to apply sixty pounds of pressure to soft tissue.

6. The device of claim 4 wherein said pressure measuring means comprises a strain gauge and a numerical display means connected to said strain gauge, said strain gauge being attached to said first jaw.

* * * * *